US011149177B2

(12) United States Patent
Tasaka et al.

(10) Patent No.: US 11,149,177 B2
(45) Date of Patent: Oct. 19, 2021

(54) WORKING FLUID FOR HEAT CYCLE

(71) Applicant: AGC Inc., Chiyoda-ku (JP)

(72) Inventors: Mai Tasaka, Chiyoda-ku (JP);
Hirokazu Takagi, Chiyoda-ku (JP);
Masato Fukushima, Chiyoda-ku (JP);
Toshiyuki Tanaka, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 55 days.

(21) Appl. No.: 16/259,342

(22) Filed: Jan. 28, 2019

(65) Prior Publication Data

US 2019/0161661 A1 May 30, 2019

Related U.S. Application Data

(63) Continuation of application No. PCT/JP2017/026796, filed on Jul. 25, 2017.

(30) Foreign Application Priority Data

Jul. 29, 2016 (JP) .............................. JP2016-150264

(51) Int. Cl.
*C09K 5/04* (2006.01)
*F25B 1/00* (2006.01)

(52) U.S. Cl.
CPC ................ *C09K 5/044* (2013.01); *C09K 5/04* (2013.01); *F25B 1/00* (2013.01); *C09K 2205/126* (2013.01); *C09K 2205/22* (2013.01); Y02P 20/10 (2015.11)

(58) Field of Classification Search
CPC .... C09K 5/044; C09K 5/04; C09K 2205/126; C09K 2205/22; C09K 2205/12; C09K 2205/102; C09K 2205/108; C09K 2205/122; C09K 5/045; Y02P 20/124; C07C 17/23; C07C 17/386; C07C 17/25; C07C 17/383; F25B 1/00
USPC .......................................................... 252/67
See application file for complete search history.

(56) References Cited

U.S. PATENT DOCUMENTS

| 4,249,412 | A | 2/1981 | Townsend, III | |
| 9,012,702 | B2 * | 4/2015 | Sun | C07C 17/25 |
| | | | | 570/157 |
| 10,138,403 | B2 * | 11/2018 | Tasaka | C10M 107/02 |
| 10,370,313 | B2 * | 8/2019 | Taniguchi | C07C 17/386 |
| 10,377,686 | B2 * | 8/2019 | Nomura | C07C 21/18 |
| 10,399,915 | B2 * | 9/2019 | Taniguchi | C07C 19/10 |
| 10,442,744 | B2 * | 10/2019 | Takeuchi | B01J 23/26 |
| 2014/0077122 | A1 * | 3/2014 | Fukushima | F25B 1/00 |
| | | | | 252/67 |
| 2014/0305667 | A1 | 10/2014 | Robin | |
| 2016/0312095 | A1 * | 10/2016 | Schultz | C09K 5/045 |
| 2018/0066170 | A1 * | 3/2018 | Tasaka | C10M 171/008 |
| 2019/0078005 | A1 * | 3/2019 | Shono | C10M 171/008 |
| 2020/0010777 | A1 * | 1/2020 | Fukushima | C10M 107/02 |
| 2020/0277245 | A1 * | 9/2020 | Shiota | C07C 17/383 |

FOREIGN PATENT DOCUMENTS

| EP | 3 395 789 A1 | 10/2018 |
| EP | 3 421 445 A1 | 1/2019 |
| JP | 10-502737 | 3/1998 |
| JP | 2007-511645 | 5/2007 |
| JP | 2008-500437 | 1/2008 |
| JP | 2008-531836 | 8/2008 |
| JP | 2014-530939 | 11/2014 |
| JP | 2015518898 | 7/2015 |
| WO | WO 96/07088 A1 | 3/1996 |
| WO | WO 2005/049761 A1 | 6/2005 |
| WO | WO 2005/119143 A2 | 12/2005 |
| WO | WO 2006/094303 A2 | 9/2006 |
| WO | WO 2012/157763 | 11/2012 |
| WO | WO 2014/080868 | 5/2014 |

OTHER PUBLICATIONS

STN CAS reg. No. 111512-60-8, Nov. 21, 1987. (Year: 1987).*
Certified Patent Document for JP 2016-033436, as found in U.S. Appl. No. 16/077,922, US 2019/0078005. (Year: 2019).*
International Search Report dated Sep. 12, 2017 in PCT/JP2017/026796 filed Jul. 25, 2017 (with English Translation).
Written Opinion dated Sep. 12, 2017 in PCT/JP2017/026796 filed Jul. 25, 2017.

* cited by examiner

*Primary Examiner* — Douglas J McGinty
(74) *Attorney, Agent, or Firm* — Oblon, McClelland, Maier & Neustadt, L.L.P.

(57) ABSTRACT

There is provided a working fluid for heat cycle that uses (Z)-1-chloro-2,3,3,3-tetrafluoropropane (HCFO-1224yd(Z)) which has a less impact on the ozone layer, has a less impact on global warming, and has excellent cycle performance, the working fluid for heat cycle having sufficiently ensured stability and having high productivity. The working fluid for heat cycle contains HCFO-1224yd(Z) and an impurity, wherein the impurity includes a specific trace component, and a total content ratio of the trace component to a total amount of the working fluid is less than 1.5 mass %.

10 Claims, 2 Drawing Sheets

WORKING FLUID FOR HEAT CYCLE

CROSS-REFERENCE TO RELATED APPLICATIONS

This application is a continuation of prior International Application No. PCT/JP2017/026796 filed on Jul. 25, 2017 which is based upon and claims the benefit of priority from Japanese Patent Application No. 2016-150264 filed on Jul. 29, 2016; the entire contents of all of which are incorporated herein by reference.

FIELD

The present invention relates to a working fluid for heat cycle.

BACKGROUND

Conventionally, chlorofluorocarbon (CFC) such as chlorotrifluoromethane (CFC-13) and dichlorodifluoromethane (CFC-12) or hydrochlorofluorocarbon (HCFC) such as chlorodifluoromethane (HCFC-22) have been used as working fluids for heat cycle, such as a chiller refrigerant, an air-conditioner refrigerant, a working fluid for a power generation system (waste heat recovery power generation or the like), a working fluid for a latent heat transport apparatus (a heat pipe or the like), and a secondary cooling medium. However CFC and HCFC have been pointed out as having an impact on the ozone layer of the stratosphere and are targets of regulation at present.

Under the above-described circumstances, as a working fluid for heat cycle, hydrofluorocarbon (HFC) such as difluoromethane (HFC-32), tetrafluoroethane (HFC-134), and pentafluoroethane (HFC-125) which have a less impact on the ozone layer, that is, have a low ozone depletion potential (ODP) are used in place of CFC and HCFC. For example, as a working fluid used in a centrifugal chiller used for cooling and heating buildings and an industrial cold water production plant, trichlorofluoromethane (CFC-11) has been replaced by 1,1,1,2-tetrafluoroethane (HFC-134a), 1,1,1,3,3-pentafluoropropane (HFC-245fa), and the like. Further, for example, R410A (pseudo-azeotropic mixture refrigerant whose mass ratio of HFC-32 and HFC-125 is 1:1) or the like is a refrigerant conventionally in wide use. However HFC has also been pointed out as having a possibility to cause global warming, and therefore, the development of a working fluid for heat cycle having a less impact on the ozone layer and having a low global warming potential (GWP) is an urgent need.

In recent years, hydrofluoroolefin (HFO), hydrochlorofluoroolefin (HCFO), and chlorofluoroolefin (CFO), and the like which have a carbon-carbon double bond easily decomposed by OH radicals present in the atmosphere have been greatly expected as a working fluid having a less impact on the ozone layer and having a low GWP. In this specification, saturated HFC is referred to as HFC and is used in distinction from HFO unless otherwise specified. Further, HFC is clearly described as saturated hydrofluorocarbon in some cases.

Among them, HCFO and CFO have a high halogen ratio in one molecule and thus are less combustible compounds, and their use as working fluids having a less environmental burden and having less flammability have been considered. For example, Patent Reference 1 (International Publication WO 2012/157763) describes a working fluid using 1-chloro-2,3,3,3-tetrafluoropropene (HCFO-1224yd). Patent Reference 1 suggests the use of HCFO-1224yd in combination with various kinds of HFC and HFO for the purpose of enhancing cycle performance and so on of this working fluid. It also describes that adding an ordinary stabilizer to the working fluid containing HCFO-1224yd can improve the stability of the working fluid.

Here, HCFO-1224yd is produced by various kinds of methods, and whichever production method is used, the resultant product contains impurities. Using HCFO-1224yd containing such impurities as it is may cause the working fluid to have insufficient stability. Further, as HCFO-1224yd, there are a Z-isomer and an E-isomer, and at the time of the production of HCFO-1224yd, the Z-isomer and the E-isomer of HCFO-1224yd are produced at the same time, and HCFO-1224yd is obtained as a mixture of these. However, a working fluid using HCFO-1224yd obtained as the mixture of the Z-isomer and the E-isomer may not have sufficient stability.

SUMMARY

Under such circumstances, the present inventors isolated a Z-isomer and an E-isomer from a mixture of 1-chloro-2,3,3,3-tetrafluoropropene (HCFO-1224yd) and confirmed that the Z-isomer is more excellent in stability than the E-isomer.

It is an object of the present invention to provide a working fluid for heat cycle using HCFO-1224yd(Z) having a less impact on the ozone layer, having a less impact on global warming, and excellent in cycle performance, whose stability is sufficiently ensured and whose productivity is high. Further, the present invention has been made in order to simplify a process of reducing impurities in impurity-containing HCFO-1224yd(Z) (hereinafter, also referred to as crude HCFO-1224yd(Z)).

Note that, in the present specification, an abbreviation of a compound being halogenated hydrocarbon is given in a parenthesis after the name of the compound, and in the present specification, the abbreviation is used instead of the name of the compound as required. Further, (E) and (Z) added to the name or abbreviation of a compound having a geometric isomer represent an E-isomer (trans-isomer) and a Z-isomer (cis-isomer) respectively. The name or abbreviation of the compound having a geometric isomer without the notation of the E-isomer or the Z-isomer means a generic name including the E-isomer, the Z-isomer, or a mixture of the E-isomer and the Z-isomer.

The present invention provides a working fluid for heat cycle, including:

(Z)-1-chloro-2,3,3,3-tetrafluoropropene ((Z)—$CF_3$—CF=CHCl, HCFO-1224yd(Z)) and an impurity including at least one kind of trace component selected from the group consisting of 1,3-dichloro-1,1,2,2,3-pentafluoropropane ($CClF_2$—$CF_2$—CHClF, HCFC-225cb), 1,1,1,2-tetrafluoropropane ($CF_3$—CHF—$CH_3$, HFC-254eb), 1,1-dichloro-2,3,3,3-tetrafluoropropene ($CF_3$—CF=$CCl_2$, CFO-1214ya), (E)-1-chloro-2,3,3,3-tetrafluoropropene ((E)-$CF_3$—CF=CHCl, HCFO-1224yd (E)), (Z)-2-chloro-1,3,3,3-tetrafluoropropene ((Z)—$CF_3$—CCl=CHF, HCFO-1224xe(Z)), (E)-2-chloro-1,3,3,3-tetrafluoropropene ((E)-$CF_3$—CCl=CHF, HCFO-1224xe (E)), 2,3,3,3-tetrafluoropropene ($CF_3$—CF=$CH_2$, HFO-1234yf), (Z)-1,3,3,3-tetrafluoropropene ((Z)—$CF_3$—CH=CHF, HFO-1234ze(Z)), (E)-1,3,3,3-tetrafluoropropene ((E)-$CF_3$—CH=CHF, HFO-1234ze(E)), 1-chloro-3,3,3-trifluoro-1-propyne ($CF_3$—CCCl), fluorohydrocarbon represented by $C_4H_4F_4$, 2-chloro-1,1,1,2-tetrafluoropropane (HCFC-244bb), 1,1,1,3,3-pentafluoropropane (HFC-245fa), 2-chloro-1,1,3,3,3-pentafluoro-1-propene (CFO-1215xc), 3,3-dichloro-1,1,1,2,2-pentafluoropropane (HCFC-225ca), 1,1,1,2,2,3,3-heptafluoropropane (FC-227ca), methanol, ethanol, acetone, chloroform, and hexane, and wherein a total content ratio of the trace component to a total amount of the working fluid for heat cycle is less than 1.5 mass %.

The working fluid for heat cycle of the present invention has a less impact on the ozone layer, has a less impact on global warming, and is excellent in cycle performance because it contains HCFO-1224yd(Z). Further, since the total content of the trace component which exists as the impurity at the time of the production of HCFO-1224yd(Z) and has an impact on the stability of the working fluid for heat cycle containing HCFO-1224yd(Z) is adjusted to less than 1.5 mass % with respect to the total amount of the working fluid for heat cycle, it is possible to obtain a working fluid for heat cycle having sufficiently ensured stability. Moreover, in the present invention, since the total content of the trace component having an impact on the stability is set to less than 1.5 mass %, it is possible to simplify the process of reducing the impurity in crude HCFO-1224yd(Z) and to produce a working fluid for heat cycle having high productivity.

DETAILED DESCRIPTION

[Working Fluid]

Figure 1:
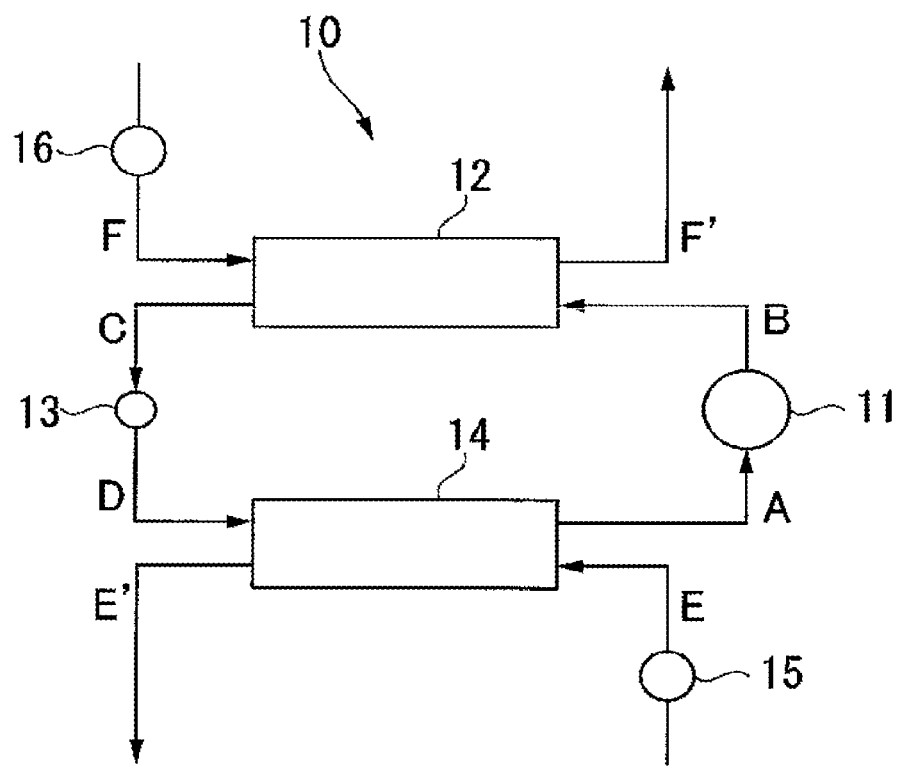
FIG. 1 is a schematic diagram illustrating a refrigeration cycle system.

A working fluid for heat cycle (hereinafter, also referred to as a "working fluid") of an embodiment of the present invention contains HCFO-1224yd(Z) and an impurity, wherein the impurity includes the following trace component (hereinafter, also referred to as the "trace component (X)"), and a total content ratio of the trace component (X) in the working fluid is less than 1.5 mass %.

The trace component (X) contained in the working fluid is at least one selected from the group consisting of HCFC-225cb, HFC-254eb, CFO-1214ya, HCFO-1224yd(E), HCFO-1224xe(Z), HCFO-1224xe(E), HFO-1234yf, HFO-1234ze(Z), HFO-1234ze(E), 1-chloro-3,3,3-trifluoro-1-propyne, fluorohydrocarbon represented by $C_4H_4F_4$, HCFC-244bb, HFC-245fa, CFO-1215xc, HCFC-225ca, FC-227ca, methanol, ethanol, acetone, chloroform, and hexane.

The working fluid of the embodiment may further contain later-described compounds (hereinafter, also referred to as "other working fluid component") in addition to HCFO-1224yd(Z) and the trace component (X).

<HCFO-1224yd(Z)>

HCFO-1224yd(Z) has, in its molecule, halogen which reduces combustibility and a carbon-carbon double bond easily decomposed by OH radicals present in the atmosphere.

HCFO-1224yd(Z) has a less impact on the ozone layer, with its ODP (a value stipulated in the Ozone Layer Protection Law or a value measured in conformity with this law) being zero. Further, it has a less impact on global warming, with its GWP (a value over 100 years stipulated in the Fourth Assessment Report (2007) of the Intergovernmental Panel on Climate Change (IPCC) or measured in conformity with the method in the report) being 5.

Further, HCFO-1224yd(Z) has an excellent capacity as a working fluid and is excellent particularly in cycle performance (for example, a coefficient of performance and a refrigerating capacity found by later-described methods).

In a case where the working fluid is composed of only HCFO-1224yd(Z) and the trace component (X), a ratio of the content of HCFO-1224yd(Z) in the working fluid can be a ratio (mass %) equal to 100 mass % minus a content ratio of the trace component (X).

Further, according to the purpose for which the working fluid is used, HCFO-1224yd(Z) and the other working fluid component may be used in appropriate combination. The content of HCFO-1224yd(Z) with respect to 100 mass % of the working fluid is preferably 10 mass % or more, more preferably 20 mass % or more, still more preferably 40 mass % or more, yet more preferably 60 mass % or more, and most preferably 90 mass % or more. The content ratio of HCFO-1224yd(Z) to 100 mass % of the working fluid excluding impurities is preferably 100 mass %. The working fluid is most preferably composed only of HCFO-1224yd(Z).

That is, the content of HCFO-1224yd(Z) with respect to 100 mass % of the working fluid is preferably 10 to 100 mass %, more preferably 20 to 100 mass %, still more preferably 40 to 100 mass %, yet more preferably 60 to 100 mass %, and most preferably 90 to 100 mass %.

For example, in a heat cycle system in which 1,1,1,3,3-heptafluoropropane (HFC-245fa) is suitably used as a working fluid, in a case where the working fluid containing HCFO-1224yd(Z) is used in place of HFC-245fa as the working fluid, the content of HCFO-1224yd(Z) with respect to 100 mass % of the working fluid excluding the impurities is preferably 40 to 100 mass %, more preferably 60 to 100 mass %, and still more preferably 80 to 100 mass %, and the working fluid is most preferably composed only of HCFO-1224yd(Z).

<Trace Component (X)>

The trace component (X) is a compound produced as a by-product at the time of the production of HCFO-1224yd(Z) and present as the impurity in a produced composition or is a solvent used in the production. The trace component (X) is specifically at least one selected from the group consisting of HCFC-225cb, HFC-254eb, CFO-1214ya, HCFO-1224yd(E), HCFO-1224xe(Z), HCFO-1224xe(E), HFO-1234yf, HFO-1234ze(Z), HFO-1234ze(E), 1-chloro-3,3,3-trifluoro-1-propyne, fluorohydrocarbon represented by $C_4H_4F_4$, HCFC-244bb, HFC-245fa, CFO-1215xc, HCFC-225ca, FC-227ca, methanol, ethanol, acetone, chloroform, and hexane.

If a total content of the trace component (X) impairs in the working fluid is 1.5 mass % or more, the trace component (X) impairs the stability of the working fluid. On the other hand, in a case where the total content of the trace component (X) is less than 1.5 mass % with respect to the total amount of the working fluid, it possible to obtain a HCFO-1224yd(Z)-containing working fluid whose stability is ensured. In view of ensuring the stability, the total content of the trace component (X) with respect to the total amount of the working fluid is preferably 1.0 mass % or less.

The content of the trace component (X) in the working fluid is preferably 4 mass ppm or more, more preferably 50 mass ppm or more, and most preferably 100 mass ppm or more with respect to the total amount of the working fluid because this can simplify the process of reducing the trace component (X) being the impurity by refining crude HCFO-1224yd(Z).

Further, some kind of compound as the trace component (X) may exhibit a specific function by being contained in appropriate amount of less than 1.5 mass % with respect to the total amount of the working fluid. For example, 1-chloro-3,3,3-trifluoro-1-propyne is a compound that enhances the stability of the working fluid containing HCFO-1224yd(Z) in a case where its content in the working fluid is less than 1.5 mass %. In view of the stability of the working fluid, the content of 1-chloro-3,3,3-trifluoro-1-propyne is preferably within a range of 0.0001 to 0.1 mass %, and more preferably 0.0001 to 0.001 mass % with respect to the total amount of the working fluid.

Further, for example, HCFC-244bb is a compound that enhances the stability of the working fluid containing HCFO-1224yd(Z) in a case where its content in the working fluid is less than 1.5 mass %. In view of the stability of the working fluid, the content of HCFC-244bb is preferably within a range of 0.001 to 0.5 mass %, and more preferably 0.01 to 0.1 mass % with respect to the total amount of the working fluid.

The trace component (X) refers to a component, including impurities in a raw material, an intermediate product, a by-product, and so on (The same applies to the below.), and contained in a crude composition, referring to, for example, a composition containing a larger amount of impurities than a refined composition, such as an outlet component from a reactor or a roughly refined product resulting from the rough refining of the outlet component (The same applies to the below.), obtained at the time of the production of HCFO-1224yd(Z). Furthermore, the trace component (X) is a component contained in a trace amount in the refined composition of HCFO-1224yd(Z) obtained by refining the crude composition by an ordinary method or is a solvent component used in the refining.

In a case where the refined composition of HCFO-1224yd(Z) is used in the working fluid, the total content of the trace component (X) in the refined composition does not necessarily have to be less than 1.5 mass %. That is, in the case where the refined composition of HCFO-1224yd(Z) is used as the working fluid as it is, the total content of the trace component (X) in the refined composition is less than 1.5 mass %, but in a case where the working fluid contains the other working fluid component, the total content of the trace component (X) in the refined composition of HCFO-1224yd(Z) may be 1.5 mass % or more, provided that the total content of the trace component (X) with respect to the total amount of the working fluid is less than 1.5 mass %.

However, since there is a possibility that the trace component (X) is brought as an impurity together with the other working fluid component at the time when the other working fluid component is blended in the working fluid, the total content of the trace component (X) in the refined composition of HCFO-1224yd(Z) used in the working fluid is preferably less than 1.5 mass %.

Hereinafter, methods to produce HCFO-1224yd(Z), impurities contained in the crude compositions obtained at the time of the production of these, and the trace components (X) contained in the HCFO-1224yd(Z) refined compositions obtained through the refining of the crude compositions will be described. The methods to produce HCFO-1224yd(Z) can be, for example, (I) a method of making 1,2-dichloro-2,3,3,3-tetrafluoropropane ($CF_3$—$CClF$—$CH_2Cl$, HCFC-234bb) undergo a dehydrochlorination reaction, and (II) a method of hydrogen-reducing 1,1-dichloro-2,3,3,3-tetrafluoropropene (CFO-1214ya).

(I) Dehydrochlorination Reaction of HCFC-234bb

In a liquid phase, HCFC-234bb is brought into contact with a base dissolved in a solvent, that is, with a base in a solution state, whereby HCFC-234bb is made to undergo the dehydrochlorination reaction represented by Formula (1).

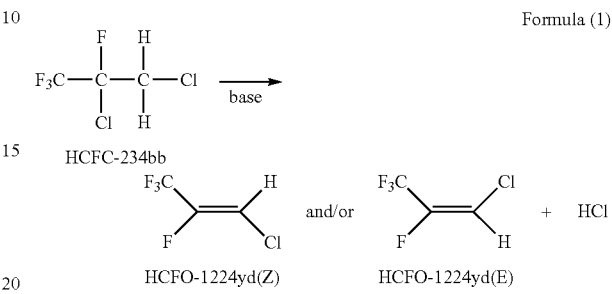

Preferably, the base is at least one selected from a group consisting of a metal hydroxide, a metal oxide, and a metal carbonate, and the solvent is water which is a solvent high in solubility and inert to the dehydrochlorination reaction. In the dehydrochlorination reaction, the reaction is preferably caused while a reaction system is made a homogeneous system state. The homogeneous system is a reaction system in which a reaction substrate (a raw material, a product, or the like) is finely dispersed by stirring or the like and is substantially uniformly distributed. Incidentally, the presence of a phase transfer catalyst during the aforesaid reaction can increase a reaction rate to improve productivity.

HCFC-234bb used when HCFO-1224yd(Z) is produced by Formula (1) is a compound well-known as a production raw material or an intermediate of a fluorine-containing compound and can be produced by a known method. For example, through a reaction of 2,3,3,3-tetrafluoropropene (HFO-1234yf) and chlorine in a solvent as represented by the following Formula (2), HCFC-234bb can be produced.

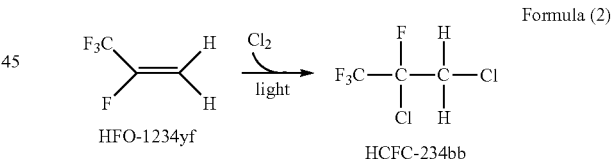

In the above dehydrochlorination reaction of HCFC-234bb, a product containing HCFO-1224yd(Z) can be obtained as the crude composition from the reactor. In a case where water is used as the solvent of the aforesaid base, by being left standing still, the obtained crude product separates into an organic layer containing HCFO-1224yd(Z) and a water layer containing the unreacted base and salt produced by the dehydrochlorination reaction, making it possible to easily separate the both.

Examples of compounds, other than HCFO-1224yd(Z), contained in the aforesaid organic layer include HCFC-234bb being the unreacted raw material, and in addition, HFO-1234yf, HCFO-1224xe, HCFO-1224yd(E), CFO-1214ya, 1,1,2-trichloro-2,3,3,3-tetrafluoropropane ($CF_3$—$CClF$—$CHCl_2$, HCFC-224ba), 1,1,1,2-tetrachloro-2,3,3,3-tetrafluoropropane ($CF_3$—$CClF$—$CCl_3$, CFC-214bb), 1-chloro-3,3,3-trifluoro-1-propyne, and HCFC-244bb.

The aforesaid organic layer is thereafter subjected to a refining treatment such as distillation, extraction, or separation for removing the impurities. In such a refining treatment, the impurities are roughly removed from the organic layer, and the refined composition composed of HCFO-1224yd(Z) and the following trace component (X) is obtained. Note that the trace component (X) in the refined composition obtained by the production method (I) is also referred to as a trace component (X1).

In the aforesaid organic layer, the phase transfer catalyst used in the dehydrochlorination reaction and the salt being a reaction by-product sometimes remain. Performing the refining treatment such as the distillation while they are left contained may lead to problems of clogging and corrosion of a device. If there are such concerns, they are desirably removed before the refining treatment, and a specific method therefor is water washing (a method of adding and mixing water to the aforesaid organic layer and thereafter recovering the organic layer by layer separation), a method of making them adsorbed by an adsorbent such as activated carbon or zeolite, or a method by the combination of these.

Further, the aforesaid organic layer sometimes contains a trace amount of moisture. Performing the refining treatment such as the distillation while the moisture is left contained may lead to a problem of the corrosion of the device. If there is such a concern, the moisture is desirably removed before the refining treatment, and a specific method therefor is, for example, a method using a moisture remover such as a drying agent (silica gel, activated alumina, zeolite, or the like).

In the above-described refining treatment, HCFC-234bb, CFO-1214ya, HCFC-224ba, CFC-214bb, and so on out of the aforesaid impurities are completely removed from the aforesaid organic layer. On the other hand, HFO-1234yf, HCFO-1224xe, HCFO-1224yd(E), 1-chloro-3,3,3-trifluoro-1-propyne, and HCFC-244bb cannot be completely removed by the above-described refining treatment and trace amounts thereof remain, for example, totally in amount of less than 1.5 mass % with respect to the total amount of the obtained refined composition, and they become the trace component (X1).

(II) Method of Hydrogen-Reducing CFO-1214Ya

As represented by Formula (3), CFO-1214ya is reduced using hydrogen in the presence of a catalyst to be converted to HFO-1234yf, and as its intermediate, HCFO-1224yd(Z) is obtained. Further, in this reduction reaction, many kinds of fluorine-containing compounds are produced as by-products besides HCFO-1224yd(Z).

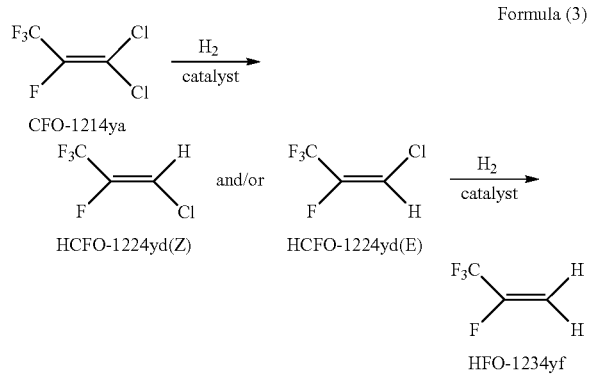

Formula (3)

A known method to produce CFO-1214ya used when HCFO-1224yd(Z) is produced by Formula (3) is, for example, to make HCFC-225ca or the like as a raw material undergo a dehydrofluorination reaction in an alkaline aqueous solution in the presence of a phase transfer catalyst or by a gas phase reaction in the presence of a catalyst such as chromium, iron, copper, or activated carbon, as represented by Formula (4).

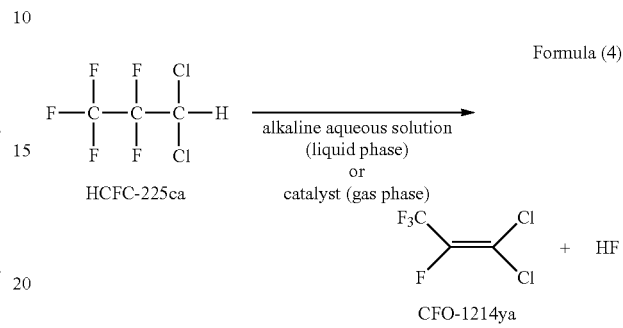

Formula (4)

Here, HCFO-1224yd(Z) can be separated from most of CFO-1214ya being the unreacted raw material and HFO-1234yf which is the final product, by typical distillation.

A fraction obtained by this distillation operation will be described as the crude composition. The crude composition contains, besides HCFO-1224yd(Z), impurities which are by-products of the aforesaid hydrogen reduction reaction, such as HFC-254eb, CFO-1215xc, 1,1,1,3,3,3-hexafluoropropane ($CF_3$—$CH_2$—$CF_3$, HFC-236fa), HFO-1234ze, fluorohydrocarbon represented by $C_4H_4F_4$, 1-chloro-1,2,2,3,3,3-hexafluoropropane ($CF_3$—$CF_2$—$CHClF$, HCFC-226ca), 1-chloro-1,1,2,2,3,3-hexafluoropropane ($CHF_2$—$CF_2$—$CClF_2$, HCFC-226cb), 1-chloro-1,3,3,3-tetrafluoropropene ($CF_3$—$CH$=$CClF$, HCFO-1224zb), 1,1,2,3-tetrafluoropropane (HFC-254ea), 2-chloro-1,1,1,2,3,3-hexafluoropropane (HCFC-226ba), HCFO-1224xe, HCFO-1224yd(E), CFO-1214ya, 1,3-dichloro-1,2,3,3-tetrafluoropropene ($CF_2Cl$—$CF$=$CClF$, CFO-1214yb), 1,2-dichloro-1,3,3,3-tetrafluoropropene ($CF_3$—$CCl$=$CClF$, CFO-1214xb), HCFC-244bb, HFC-245fa, HCFC-225ca, and FC-227ca.

Examples of the fluorohydrocarbon represented by $C_4H_4F_4$ include 1,3,4,4-tetrafluoro-1-butene ($CF_2H$—$CHF$—$CH$=$CHF$) and 3,4,4,4-tetrafluoro-1-butene ($CF_3$—$CHF$—$CH$=$CH_2$), 1,1,2,3-tetrafluoro-1-butene ($CH_3$—$CHF$—$CF$=$CF_2$).

Since the aforesaid impurities contained in the crude composition include a compound that forms an azeotropic composition or an azeotropic-like composition with HCFO-1224yd(Z), a refining method by extractive distillation is effective as a refining method to obtain the refined composition. The extractive distillation is a method of adding another component to a composition composed of a plurality of components to change a relative volatility of a predetermined component, thereby facilitating the distillation separation, and the other component mentioned here is called an extraction solvent. As the extraction solvent of HCFO-1224yd(Z), methanol, acetone, hexane, ethanol, CFO-1214ya, chloroform, HCFC-225cb, or the like is used.

In the refining treatment by the extractive distillation, the impurities are mostly removed from the crude composition, and the refined composition composed of HCFO-1224yd(Z) and the following trace component (X) is obtained. Note that the trace component (X) in the refined composition obtained by the production method (II) is also referred to as a trace component (X2).

In the aforesaid refining treatment, HFC-236fa, HCFC-226ca, HCFC-226cb, HCFO-1224zb, HFC-254ea, HCFC-226ba, CFO-1214ya, CFO-1214yb, CFO-1214xb, and so on out of the aforesaid impurities are completely removed from the crude composition. On the other hand, CFO-1215xc, HFC-254eb, HFO-1234ze, fluorohydrocarbon represented by $C_4H_4F_4$, HCFO-1224xe, HCFO-1224yd(E), HCFC-244bb, HFC-245fa, HCFC-225ca, and FC-227ca cannot be completely removed in the aforesaid refining treatment and trace amounts of these remain. Further, a trace amount of methanol, acetone, hexane, ethanol, CFO-1214ya, chloroform, HCFC-225cb, or the like used as the extraction solvent sometimes remains.

Thus, the trace component (X2) can include CFO-1215xc, HFC-254eb, HFO-1234ze, fluorohydrocarbon represented by $C_4H_4F_4$, HCFO-1224xe, HCFO-1224yd(E), HCFC-244bb, HFC-245fa, HCFC-225ca, FC-227ca, methanol, acetone, hexane, ethanol, CFO-1214ya, chloroform, HCFC-225cb, and so on. The content of the trace component (X2) in the refined composition is less than 1.5 mass %.

Methanol, acetone, hexane, ethanol, CFO-1214ya, chloroform, HCFC-225cb, or the like used as the extraction solvent sometimes remains in the composition obtained after the extractive distillation with content of 1.5 mass % or more. In this case, the content of these extraction solvents is reduced by an appropriate method such that the content as the total amount of the trace component (X2) in the obtained refined composition becomes less than 1.5 mass %. For example, in a case where the remaining amount of the methanol in the composition obtained after the extractive distillation is 1.5 mass % or more, it is possible to reduce the content of the methanol to the aforesaid range by two-layer separation after it is mixed with water.

<Other Working Fluid Component>

The working fluid of the present invention can further contain the other working fluid component besides HCFO-1224yd(Z) and the impurities. The other working fluid component is preferably at least one selected from the group consisting of hydrofluorocarbon (HFC), hydrofluoroolefin (HFO), and hydrochlorofluoroolefin (HCFO) (except HCFO-1224yd(Z) and the trace component (X)).

Examples of HFC except the trace component (X) include difluoromethane (HFC-32), 1,1-difluoroethane (HFC-152a), 1,1,1-trifluoroethane (HFC-143a), 1,1,2,2-tetrafluoroethane (HFC-134), 1,1,1,2-tetrafluoroethane (HFC-134a), and pentafluoroethane (HFC-125) because these have a less impact on the ozone layer and are excellent in cycle performance. As HFC, one kind of these may be used alone or two kinds or more of these may be used in combination.

Examples of HFO include 2-fluoropropene (HFO-1261yf), 1,1,2-trifluoropropene (HFO-1243yc), (E)-1,2,3,3,3-pentafluoropropene (HFO-1225ye(E)), (Z)-1,2,3,3,3-pentafluoropropene (HFO-1225ye(Z)), 3,3,3-trifluoropropene (HFO-1243zf), (Z)-1,1,1,4,4,4-hexafluoro-2-butene (HFO-1336mzz(Z)), and (E)-1,1,1,4,4,4-hexafluoro-2-butene (HFO-1336mzz(E)) because they have a less impact on the ozone layer and are excellent in cycle properties. As HFO, one kind of these may be used alone or two kinds or more of these may be used in combination.

Examples of HCFO include 1-chloro-2,2-difluoroethylene (HCFO-1122), 1,2-dichlorofluoroethylene (HCFO-1121), 1-chloro-2-fluoroethylene (HCFO-1131), and 2-chloro-3,3,3-trifluoropropene (HCFO-1233xf). As HCFO, one kind of these may be used alone or two kinds or more of these may be used in combination.

The total content of the other working fluid component in the working fluid of the present invention can be an amount equal to 100 mass % minus the total content of HCFO-1224yd(Z) and the impurities. Specifically, the total content of the other working fluid component can be 0 to 90 mass % with respect to the total amount of the working fluid.

<Other Impurities>

Impurities (other impurities) described below except the aforesaid trace component (X), if contained in the working fluid, may cause a problem when the working fluid is used in the heat cycle system. There is a possibility that these impurities are brought also from a later-described lubricating oil used with the working fluid in the heat cycle system or enter from the outside during the operation of the heat cycle system, and therefore they are components whose content in the working fluid is desirably reduced as much as possible.

(Acid Content)

An acid content, if present in the heat cycle system, has an adverse effect such as the decomposition of the working fluid and the lubricating oil. The acid content in the working fluid is preferably less than 1 mass ppm, and especially preferably 0.8 mass ppm or less in terms of the concentration measured by an acid-base titration method. Note that the concentration of a given component in the working fluid means a mass ratio of the content of this component to the total amount of the working fluid.

(Chlorine Ion)

Chlorine, if present in the heat cycle system, has adverse effects such as the production of a deposit due to its reaction with metal, the abrasion of a bearing part, and the decomposition of the working fluid and the lubricating oil. Chlorine is present as chlorine ions in the working fluid. The concentration of the chlorine ions in the working fluid is preferably 3 mass ppm or less, and especially preferably 1 mass ppm or less in terms of the chlorine ion concentration measured by silver nitrate turbidimetry.

(Evaporation Residue)

An evaporation residue remaining after the working fluid is evaporated is problematic because it causes the clogging of a pipe part and the like when the working fluid is used in the heat cycle system. The evaporation residue of the working fluid is preferably 15 mass ppm or less, and especially preferably 10 mass ppm or less with respect to the total amount of the working fluid, in terms of an amount of the evaporation residue remaining after the 100 g of working fluid is treated at 40° C. for sixty minutes.

(Moisture)

Moisture, if mixed into the heat cycle system, causes problems such as its freezing in a capillary tube, the hydrolysis of the working fluid and the lubricating oil, material deterioration due to the acid content produced in the system, the production of contaminants, and so on. The content of the moisture in the working fluid is preferably 20 mass ppm or less, and especially preferably 15 mass ppm or less with respect to the total amount of the working fluid, in terms of the moisture content measured by the Karl Fischer coulometric titration method.

(Air)

Air (consisting of nitrogen of about 80% by volume, oxygen of about 20% by volume), if mixed into the heat cycle system, has adverse effects such as a heat transfer failure in a condenser and an evaporator, and a working pressure rise, and therefore, it is necessary to reduce the mixture of the air as much as possible. In particular, oxygen in the air reacts with the working fluid and the lubricating oil to promote their decomposition. The air concentration in the working fluid is preferably less than 15000 mass ppm, and especially preferably 8000 mass ppm or less in terms of the air concentration measured by gas chromatography.

[Application to Heat Cycle System]

The working fluid of the present invention is useful as a working fluid for heat cycle system that not only has a less impact on the ozone layer, has a less impact on global warming, and is excellent in cycle performance but also has ensured stability.

<Composition for Heat Cycle System>

The working fluid of the present invention is typically mixed with a lubricating oil when applied to a heat cycle system and the mixture is usable as a composition for heat cycle system. The composition for heat cycle system containing the working fluid of the present invention and the lubricating oil may further contain, besides these, known additives such as a stabilizer and a leakage detection substance.

(Lubricating Oil)

In the heat cycle system, the above-described working fluid may be used as a mixture with the lubricating oil. As the lubricating oil, a known lubricating oil used in heat cycle systems is adoptable. The lubricating oil is contained together with the aforesaid working fluid in the composition for heat cycle system, circulates in the heat cycle system, and functions as a lubricating oil especially in a compressor in the heat cycle system. In the heat cycle system, the lubricating oil is preferably one that has a sufficient lubricating ability, ensures the hermeticity of the compressor and at the same time has sufficient compatibility with the working fluid under low-temperature conditions. From this point of view, the dynamic viscosity of the lubricating oil at 40° C. is preferably 1 to 750 mm$^2$/s, and more preferably to 1 to 400 mm$^2$/s. Further, its dynamic viscosity at 100° C. is preferably 1 to 100 mm$^2$/s, and more preferably 1 to 50 mm$^2$/s.

Examples of the lubricating oil include an ester-based lubricating oil, an ether-based lubricating oil, a fluorine-based lubricating oil, a hydrocarbon-based synthetic oil, and a mineral oil.

The ester-based lubricating oil is an ester compound that has an ester bond in its molecule and that is oily, preferably has the aforesaid dynamic viscosity. Examples of the ester-based lubricating oil include dibasic acid ester, polyol ester, complex ester, and polyol carbonate ester.

The dibasic acid ester is preferably an ester of dibasic acid having 5 to 10 carbon atoms (glutaric acid, adipic acid, pimelic acid, suberic acid, azelaic acid, sebacic acid, or the like) and monohydric alcohol having 1 to 15 carbon atoms that has a straight-chain alkyl group or a branched alkyl group (methanol, ethanol, propanol, butanol, pentanol, hexanol, heptanol, octanol, nonanol, decanol, undecanol, dodecanol, tridecanol, tetradecanol, pentadecanol, 2-ethylhexanol, isodecyl alcohol, 3-ethyl-3-hexanol, or the like). Specific examples thereof include ditridecyl glutarate, di(2-ethylhexyl)adipate, diisodecyl adipate, ditridecyl adipate, and di(3-ethyl-3-hexyl)sebacate.

The polyol ester is an ester synthesized from polyhydric alcohol and fatty acid (carboxylic acid).

The polyol ester is preferably an ester of diol (ethylene glycol, 1,3-propanediol, propylene glycol, 1,4-butanediol, 1,2-butanediol, 1,5-pentanediol, neopentyl glycol, 1,7-heptanediol, 1,12-dodecanediol, or the like) or polyol having 3 to 20 hydroxyl groups (trimethylolethane, trimethylolpropane, trimethylolbutane, pentaerythritol, glycerin, sorbitol, sorbitan, sorbitol glycerin condensate, or the like) and fatty acid having 6 to 20 carbon atoms (straight-chain or branched fatty acid or fatty acid having quaternary a carbon atom such as hexanoic acid, heptanoic acid, octanoic acid, 2-ethylhexanoic acid, pelargonic acid, decanoic acid, undecanoic acid, dodecanoic acid, eicosanoic acid, or oleic acid). The polyol ester may have a free hydroxyl group.

The polyol ester is more preferably an ester (trimethylolpropane tripelargonate, pentaerythritol-2-ethylhexanoate, pentaerythritol tetrapelargonate, or the like) of hindered alcohol (neopentyl glycol, trimethylolethane, trimethylolpropane, trimethylolbutane, pentaerythritol or the like).

The complex ester is a combination (complex) of a plurality of kinds of esters. The complex ester oil is an oligoester of at least one selected from fatty acid and dibasic acid, and polyol. Examples of the fatty acid, the dibasic acid, and the polyol include the same ones as those listed in the dibasic acid ester and the polyol ester.

The polyol carbonate ester is an ester of carbonic acid and polyol, or a ring-opening polymer of a cyclic alkylene carbonate. Examples of the polyol include the same diols, polyols, and so on as those listed in the aforesaid polyol ester.

The ether-based lubricating oil is an ether compound that has an ether bond in its molecule and that is oily, preferably, has the aforesaid dynamic viscosity. Examples of the ether-based lubricating oil include polyalkylene glycol and polyvinyl ether.

The polyalkylene glycol is a compound having a plurality of oxyalkylene units, in other words, is a polymer or a copolymer of alkylene oxide.

Examples of the polyalkylene glycol include polyalkylene polyols obtained by, for example, a method of polymerizing alkylene oxide having 2 to 4 carbon atoms (ethylene oxide, propylene oxide, or the like), using water, alkane monool, the aforesaid diol, the aforesaid polyol, or the like as an initiator, and those in which hydroxyl groups of the above are partly or entirely turned into alkyl ether.

The number of kinds of the oxyalkylene units in one molecule of the polyalkylene glycol may be one or may be two or more. The polyalkylene glycol is preferably one including at least an oxypropylene unit in one molecule, and is more preferably polypropylene glycol or a dialkyl ether of polypropylene glycol.

The polyvinyl ether is a polymer having at least a polymer unit derived from a vinyl ether monomer.

Examples of the polyvinyl ether include a polymer of a vinyl ether monomer, a copolymer of a vinyl ether monomer and a hydrocarbon monomer having an olefinic double bond, and a copolymer of a vinyl ether monomer and a vinyl ether monomer having a plurality of oxyalkylene units. Alkylene oxide forming the oxyalkylene unit is preferably any of those exemplified in the polyalkylene glycol. These polymers each may be a block or random copolymer.

The vinyl ether monomer is preferably alkyl vinyl ether, and its alkyl group is preferably an alkyl group having 6 or less of carbon atoms. Further, as the vinyl ether monomer, one kind may be used alone or two kinds or more may be used in combination. Examples of the hydrocarbon monomer having the olefinic double bond include ethylene, propylene, various kinds of butenes, various kinds of pentenes, various kinds of hexenes, various kinds of heptenes, various kinds of octenes, diisobutylene, triisobutylene, styrene, α-methylstyrene, and various kinds of alkyl-substituted styrenes. As the hydrocarbon monomer having the olefinic double bond, one kind may be used alone or two kinds or more may be used in combination.

The fluorine-based lubricating oil is a fluorine-containing compound that has a fluorine atom in its molecule and that is oily, preferably, has the aforesaid dynamic viscosity.

Examples of the fluorine-based lubricating oil include a compound in which a hydrogen atom of a later-described mineral oil or hydrocarbon-based synthetic oil (for example, polyα-olefin, alkyl benzene, alkyl naphthalene, or the like) is replaced by a fluorine atom, a perfluoropolyether oil, and a fluorinated silicone oil.

The mineral oil is obtained by refining a lubricating oil fraction obtained through atmospheric distillation or reduced-pressure distillation of a crude oil, by an appropriate combination of refining treatments (solvent deasphalting, solvent extraction, hydrocracking, solvent dewaxing, contact dewaxing, hydrorefining, clay treatment, and so on). Examples of the mineral oil include a paraffinic mineral oil and a naphthenic mineral oil.

The hydrocarbon-based synthetic oil is a synthesized compound whose molecule is composed only of a carbon atom and a hydrogen atom and that is oily, preferably, has the aforesaid dynamic viscosity. Examples of the hydrocarbon-based synthetic oil include poly α-olefin, alkyl benzene, and alkyl naphthalene.

As the lubricating oil, one kind may be used alone or two kinds or more may be used in combination.

In a case where the mixture of the working fluid and the lubricating oil is used, an amount of the lubricating oil used may be any, provided that it falls within a range not causing a great reduction in the effect of the present invention, and may be appropriately decided according to its use, a type of the compressor, and so on. The total mass ratio of the lubricating oil in the composition for heat cycle system to the total mass, that is, 100 parts by mass, of the working fluid is preferably 10 to 100 parts by mass, and more preferably 20 to 50 parts by mass.

(Stabilizer)

The stabilizer is a component which improves the stability of the working fluid against heat and oxidation. Examples of the stabilizer include an oxidation resistance improver, a heat resistance improver, and a metal deactivator.

The oxidation resistance improver is a stabilizer that stabilizes the working fluid by inhibiting the decomposition of the working fluid mainly due to oxygen, under a condition where the working fluid is repeatedly compressed and heated in the heat cycle system.

Examples of the oxidation resistance improver include N,N'-diphenylphenylenediamine, p-octyldiphenylamine, p,p'-dioctyldiphenylamine, N-phenyl-1-naphthyl amine, N-phenyl-2-naphthylamine, N-(p-dodecyl)phenyl-2-naphthylamine, di-1-naphthylamine, di-2-naphthylamine, N-alkylphenothiazine, 6-(t-butyl)phenol, 2,6-di-(t-butyl)phenol, 4-methyl-2,6-di-(t-butyl)phenol, and 4,4'-methylenebis(2,6-di-t-butylphenol). As the oxidation resistance improver, one kind may be used alone, or two kinds or more may be used in combination.

The heat resistance improver is a stabilizer that stabilizes the working fluid by inhibiting the decomposition of the working fluid mainly due to heat, under a condition where the working fluid is repeatedly compressed and heated in the heat cycle system. Examples of the heat resistance improver include the same ones as those listed as the examples of the oxidation resistance improver. As the heat resistance improver, one kind may be used alone, or two kinds or more may be used in combination.

The metal deactivator is used for the purpose of preventing a metal material in the heat cycle system from having an adverse effect on the working fluid and the lubricating oil or protecting the metal material from the working fluid and the lubricating oil. Specific examples thereof include a chemical agent that forms a coating film on a surface of the metal material.

Examples of the metal deactivator include imidazole, benzimidazole, 2-mercaptobenzothiazole, 2,5-dimercaptothiadiazole, salicylidine-propylenediamine, pyrazole, benzotriazole, tolyltriazole, 2-methylbenzimidazole, 3,5-dimethylpyrazole, methylenebis-benzotriazole, and organic acid, or esters of these, primary, secondary, or tertiary aliphatic amine, amine salt of organic acid or inorganic acid, a heterocyclic nitrogen-containing compound, and amine salt of alkyl acid phosphate, or derivatives of these.

A total mass ratio of the stabilizer to the total mass (100 mass %) of the working fluid in the composition for heat cycle system may be any, provided that it falls within a range not causing a great reduction in the effect of the present invention, and is preferably 5 mass % or less, and more preferably 1 mass % or less.

(Known Additives Such as Leakage Detection Substance)

The leakage detection substance refers to a substance in general that is added for the purpose of facilitating the detection of the working fluid and so on, using smell, fluorescence, or the like when the working fluid and so on leak from the heat cycle system.

Examples of the leakage detection substance include an ultraviolet fluorescent dye, an odor gas, and an odor masking agent. Examples of the ultraviolet fluorescent dye include known ultraviolet fluorescent dyes such as those described in the specification of U.S. Pat. No. 4,249,412, JP-A-H10-502737, JP-A-2007-511645, JP-A-2008-500437, and JP-A-2008-531836.

The odor masking agent refers to a substance in general such as a compound or a perfume that is added in a case where the working fluid, the lubricating oil, and a later-described solubilizing agent have an unpleasant odor, for the purpose of improving the odor while maintaining properties of themselves. Examples of the odor masking agent include known perfumes such as those described in JP-A-2008-500437 and JP-A-2008-531836.

In a case where the leakage detection substance is used, the solubilizing agent which improves solubility of the leakage detection substance in the working fluid may be used. Examples of the solubilizing agent include those described in JP-A-2007-511645, JP-A-2008-500437, and JP-A-2008-531836.

A total mass ratio of the leakage detection substance to the total mass (100 mass %) of the working fluid in the composition for heat cycle system may be any, provided that it falls within a range not causing a great reduction in the effect of the present invention, and is preferably 2 mass % or less, and more preferably 0.5 mass % or less.

<Heat Cycle System>

The heat cycle system to which the working fluid of the present invention is applied may be a heat pump system that uses hot heat obtained in a condenser or may be a refrigeration cycle system that uses cold heat obtained in an evaporator. The heat cycle system of the present invention may be of a flooded evaporator type or of a direct expansion type. In the heat cycle system of the present invention, a substance, other than the working fluid, that is heat-exchanged with the working fluid is preferably water or air.

The heat cycle system to which the working fluid of the present invention is applied will be hereinafter described with reference to the drawings, taking a refrigeration cycle system as an example. The refrigeration cycle system is a system in which the working fluid removes thermal energy from a load fluid in an evaporator to cool the load fluid, thereby cooling it to a lower temperature.

The refrigeration cycle system 10 illustrated in FIG. 1 is a system including, schematically: a compressor 11 which compresses a working fluid vapor A into a high-temperature and high-pressure working fluid vapor B; a condenser 12 which cools the working fluid vapor B discharged from the compressor 11 to liquefy it into a low-temperature and high-pressure working fluid C; an expansion valve 13 which expands the working fluid C discharged from the condenser 12 into a low-temperature and low-pressure working fluid D; an evaporator 14 which heats the working fluid D discharged from the expansion valve 13 into the high-temperature and low-pressure working fluid vapor A; a pump 15 which supplies a load fluid E to the evaporator 14; and a pump 16 which supplies a fluid F to the condenser 12.

In the refrigeration cycle system 10, the following cycle is repeated.

(i) The working fluid vapor A discharged from the evaporator 14 is compressed into the high-temperature and high-pressure working fluid vapor B in the compressor 11.

(ii) The working fluid vapor B discharged from the compressor 11 is cooled by the fluid F to be liquefied into the low-temperature and high-pressure working fluid C in the condenser 12. At this time, the fluid F is heated into a fluid F', which is then discharged from the condenser 12.

(iii) The working fluid C discharged from the condenser 12 is expanded into the low-temperature and low-pressure working fluid D in the expansion valve 13.

(iv) The working fluid D discharged from the expansion valve 13 is heated by the load fluid E into the high-temperature and low-pressure working fluid vapor A in the evaporator 14. At this time, the load fluid E is cooled into a load fluid E', which is then discharged from the evaporator 14.

The refrigeration cycle system 10 is a cycle system involving an adiabatic and isentropic change, an isenthalpic change, and an isobaric change. A state change of the working fluid, when superimposed on a pressure-enthalpy line (curve) in FIG. 2, can be depicted as a trapezoid having vertexes A, B, C and D.

Figure 2:
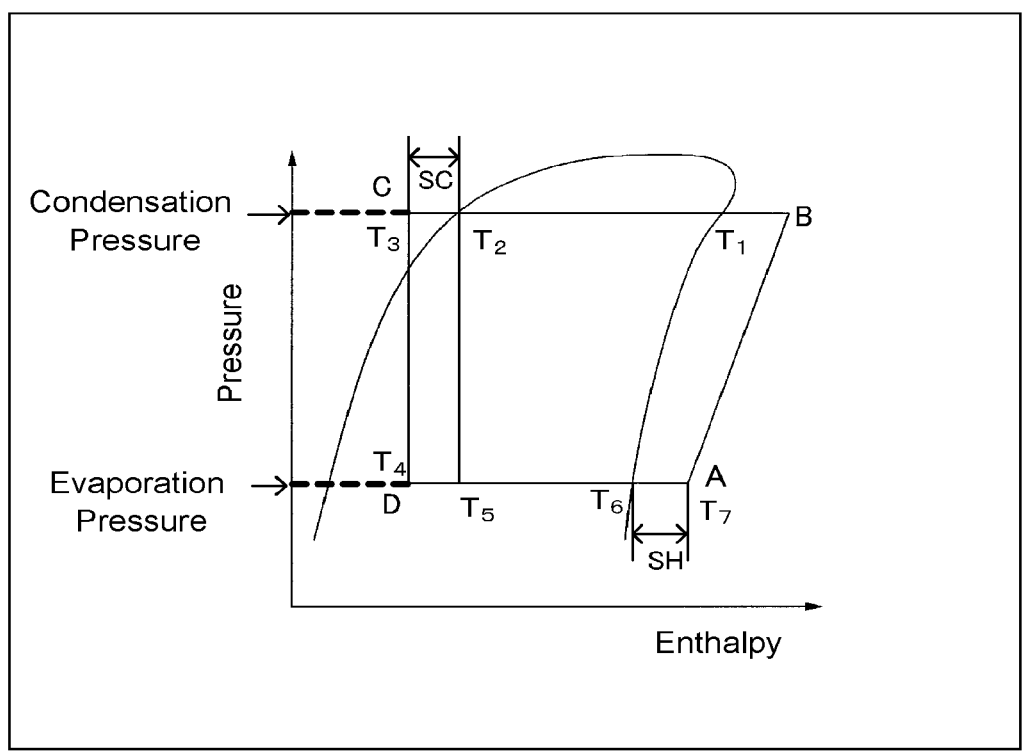
FIG. 2 is a cycle chart in which a state change of a working fluid in the refrigeration cycle system in FIG. 1 is superimposed on a pressure-enthalpy line.

An AB process is a process where adiabatic compression is performed in the compressor 11 to turn the high-temperature and low-pressure working fluid vapor A into the high-temperature and high-pressure working fluid vapor B, and is represented by the AB line in FIG. 2.

A BC process is a process where isobaric cooling is performed in the condenser 12 to turn the high-temperature and high-pressure working fluid vapor B into the low-temperature and high-pressure working fluid C, and is represented by the BC line in FIG. 2. A pressure at this time is a condensing pressure. Out of points of intersection of the pressure-enthalpy line and the BC line, a point $T_1$ of intersection on a high-enthalpy side is a condensing temperature, and a point $T_2$ of intersection on a low-enthalpy side is a condensation boiling temperature.

A CD process is a process where isenthalpic expansion is performed in the expansion valve 13 to turn the low-temperature and high-pressure working fluid C into the low-temperature and low-pressure working fluid D, and is represented by the CD line in FIG. 2. Incidentally, let a temperature in the low-temperature and high-pressure working fluid C be $T_3$, $T_2$-$T_3$ is a degree of subcooling (hereinafter, represented by "SC" as required) of the working fluid in the (i) to (iv) cycle.

A DA process is a process where isobaric heating is performed in the evaporator 14 to return the low-temperature and low-pressure working fluid D to the high-temperature and low-pressure working fluid vapor A, and is represented by the DA line in FIG. 2. A pressure at this time is an evaporating pressure. Out of points of intersection of the pressure-enthalpy line and the DA line, a point $T_6$ of intersection on a high-enthalpy side is an evaporation temperature. Let a temperature of the working fluid vapor A be $T_7$, $T_7$-$T_6$ is a degree of superheating (hereinafter, represented by "SH" as required) of the working fluid in the (i) to (iv) cycle. Note that $T_4$ represents a temperature of the working fluid D.

Here, the cycle performance of the working fluid can be evaluated from, for example, a refrigerating capacity (hereinafter, represented by "Q" as required) and a coefficient of performance (hereinafter, represented by "COP" as required) of the working fluid. Q and COP of the working fluid are found from the following Formulas (A) and (B) respectively, using enthalpies $h_A$, $h_B$, $h_C$, and $h_D$ of the working fluid in respective states A (after-evaporation, at high-temperature and low-pressure), B (after-compression, at high-temperature and high-pressure), C (after-condensation, at low-temperature and high-pressure), and D (after-expansion, at low-temperature and low-pressure).

$$Q = h_A - h_D \tag{A}$$

$$\text{COP} = Q/\text{compression work} = (h_A - h_D)/h_B - h_A \tag{B}$$

Note that COP means efficiency in the refrigeration cycle system, and COP having a larger value indicates that a larger output, for example, Q can be obtained with a smaller input, for example, electric energy necessary for operating the compressor.

Q means a capacity to cool the load fluid, and larger Q indicates that more works can be done in the same system. In other words, having larger Q indicates that intended performance can be obtained with a smaller amount of the working fluid, enabling the downsizing of the system.

Specific examples of the heat cycle system include freezing and cold-storage equipment, an air-conditioning apparatus, a power generation system, a heat transport apparatus, and a secondary cooling machine. Among all, the heat cycle system to which the working fluid of the present invention is applied is preferably used as an air-conditioning apparatus often installed outdoors or the like because the heat cycle system can exhibit stable cycle performance even in a high-temperature working environment. The heat cycle system of the present invention is also preferably used as freezing and cold-storage equipment.

The power generation system is preferably a power generation system using a Rankine cycle system. Specific examples of the power generation system include a system in which the working fluid is heated in an evaporator by geothermal energy, solar heat, waste heat in a mid to high-temperature range of about 50 to 200° C., or the like, the working fluid turned into a high-temperature and high-pressure vapor is adiabatically expanded in an expansion apparatus, and a generator is driven by a work generated by the adiabatic expansion to generate power.

Further, the heat cycle system may be a heat transport apparatus. The heat transport apparatus is preferably a latent heat transport apparatus. Examples of the latent heat transport apparatus include a heat pipe which performs latent heat transport by using phenomena such as the evaporation, boiling, and condensation of the working fluid sealingly filled in the apparatus, and a two-phase closed thermosiphon apparatus. The heat pipe is applied to a relatively small cooling apparatus such as a cooling apparatus of a heat generating part of a semiconductor element or an electronic device. The two-phase closed thermosiphon is widely used for a gas-gas heat exchanger, thawing acceleration and freezing prevention of a road, and so on because it does not require a wig and has a simple structure.

Specific examples of the freezing and cold-storage equipment include a showcase (a built-in-type showcase, a separate-type showcase, and the like), a refrigerator for industrial use, a vending machine, and an ice machine, and the like.

Specific examples of the air-conditioning apparatus include a room air-conditioner, a package air-conditioner (a store package air-conditioner, a building package air-conditioner, a facility package air-conditioner, and the like), a heat source equipment chilling unit, a gas engine heat pump, a train air-conditioner, and an automotive air-conditioner.

Examples of the heat source equipment chilling unit include a positive displacement chiller and a centrifugal chiller, and the centrifugal chiller described next is preferable because it is filled with a large amount of the working fluid and can provide a more remarkable effect of the present invention.

Here, the centrifugal chiller is a chiller using a centrifugal compressor. The centrifugal chiller is a kind of a vapor-compression type chiller. The centrifugal compressor is provided with an impeller and compresses the working fluid by discharging the working fluid to an outer peripheral part by the rotating impeller. The centrifugal chiller is used in a cold water production plant of a semiconductor factory and a petrochemical factory in addition to being used for air-conditioning in office buildings, district air-conditioning, and air-conditioning in hospitals.

The centrifugal chiller may be either of a low-pressure type or of a high-pressure type, and is preferably a low-pressure type centrifugal chiller. Note that the low-pressure type refers to, for example, a centrifugal chiller that uses a working fluid to which the High Pressure Gas Safety Act is not applied, such as trichlorofluoromethane (CFC-11), 2,2-dichloro-1,1,1-trifluoroethane (HCFC-123), or HFC-245fa, that is, uses a working fluid not falling under the category of "liquefied gas, the pressure of which is not less than 0.2 MPa at its normal operating temperature and the pressure of which is currently not less than 0.2 MPa, or liquefied gas, the temperature of which is 35° C. or lower in the case where its pressure is 0.2 MPa or more".

Incidentally, when the heat cycle system is operated, in order to avoid the occurrence of problems due to the mixture of moisture and the mixture of a non-condensing gas such as oxygen, it is preferable to provide a means for inhibiting the mixture of these.

The moisture, if mixed into the heat cycle system, may cause the aforesaid problems, and is likely to cause the problems especially when the heat cycle system is used at low temperatures. In particular, in a case where the lubricating oil is polyalkylene glycol, polyol ester, or the like, it has very high hygroscopicity and is likely to undergo a hydrolysis reaction, leading to deteriorated properties as the lubricating oil, which is a great factor to impair the long-term reliability of the compressor. Therefore, in order to inhibit the hydrolysis reaction of the lubricating oil, it is necessary to control the moisture concentration in the heat cycle system.

Examples of a method to control the moisture concentration in the heat cycle system include a method using a moisture remover such as a drying agent (silica gel, activated alumina, zeolite, or the like). The drying agent is preferably brought into contact with a liquid composition for heat cycle system from a viewpoint of dehydration efficiency. For example, the drying agent is brought into contact with the composition for heat cycle system, preferably by being disposed at an outlet of the condenser or an inlet of the evaporator.

The drying agent is preferably a zeolite-based drying agent from a viewpoint of chemical reactivity of the drying agent and the composition for heat cycle system and a hygroscopic capacity of the drying agent.

In a case where a lubricating oil higher in moisture absorption than a conventional mineral-based lubricating oil is used, the zeolite-based drying agent is preferably a zeolite-based drying agent whose main component is a compound represented by the following Formula (C) because it has an excellent hygroscopic capacity.

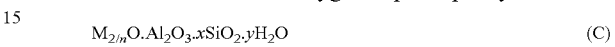

$$M_{2/n}O \cdot Al_2O_3 \cdot xSiO_2 \cdot yH_2O \qquad (C)$$

Where M is a group 1 element such as Na or K or a group 2 element such as Ca, n is the valency of M, and x and y are values determined by a crystal structure. Varying M can adjust a pore size.

In the selection of the drying agent, the pore size and breaking strength are important. In a case where a drying agent having a pore size larger than molecular sizes of various components (hereinafter, "working fluid and so on") such as the working fluid contained in the composition for heat cycle, the working fluid and so on are adsorbed in the drying agent, and as a result, a chemical reaction of the working fluid and so on and the drying agent takes place, leading to undesirable phenomena such as the generation of a non-condensing gas, and strength deterioration and adsorption capacity deterioration of the drying agent.

Therefore, as the drying agent, a zeolite-based drying agent with a small pore size is preferably used. The pore size is preferably 10 angstroms or less, and a sodium-potassium A type synthetic zeolite having a pore size of 3.5 angstroms or less is especially preferable. Employing the sodium-potassium synthetic A type zeolite having a pore size smaller than the molecular sizes of the working fluid and so on makes it possible to selectively adsorb and remove only moisture in the heat cycle system without any adsorption of the working fluid and so on. In other words, since the adsorption of the working fluid and so on to the drying agent is unlikely to occur, thermal decomposition is unlikely to occur, and as a result, it is possible to inhibit the deterioration of materials forming the heat cycle system and the generation of contaminants.

Too small size of a zeolite-based drying agent causes the clogging in a valve and a pipe small part of the heat cycle system, and too large size of a zeolite-based drying agent is low in drying capacity, and therefore a representative particle size value is preferably about 0.5 to 5 mm. Its shape is preferably granular or cylindrical.

The zeolite-based drying agent can be formed into an arbitrary shape by compacting powder zeolite by a binder (bentonite or the like). Another drying agent (silica gel, activated alumina, or the like) may be co-used, provided that the zeolite-based drying agent forms a major part.

Chlorine, if present in the heat cycle system, has adverse effects such as the production of a deposit due to its reaction with metal, the abrasion of a bearing part, and the decomposition of the working fluid and the lubricating oil, as described in the working fluid above. The chlorine concentration in the heat cycle system is preferably 100 ppm or less, and especially preferably 50 ppm or less in terms of a mass ratio to the working fluid.

Further, the non-condensing gas, if mixed in the heat cycle system, has adverse effects such as a heat transfer failure in the condenser and the evaporator, and a working pressure rise, and therefore, it is necessary to reduce the mixture as much as possible, as described in the working fluid above. In particular, oxygen which is one of the non-condensing gases reacts with the working fluid and the lubricating oil to promote their decomposition. In the heat cycle system, the non-condensing gas concentration in a gas phase part of the working fluid is preferably 1.5% by volume or less, and especially preferably 0.5% by volume or less in terms of volume percentage to the working fluid.

EXAMPLES

Hereinafter, the present invention will be described by Examples, and the present invention is not limited to the following Examples. Examples 1 to 4 and 7 to 16 are Examples, and Examples 5 and 6 are Comparative Examples.

Examples 1 to 16

Working fluids 1 to 16 each containing HCFO-1224yd(Z) and the trace component (X1) or the trace component (X2) whose ratios are given in Table 1 and further containing other impurities whose ratios are given in Table 1 were prepared. Components common to the trace component (X1) and the trace component (X2) are given in Table as "Common to (X1) (X2)".

The Examples 1, 3 and 5 are working fluids each obtained by distillation refining of a crude composition obtained through (I) the dehydrochlorination reaction of HCFC-234bb described above.

The trace component (X1) includes HFO-1234yf, HCFO-1224xe, HCFO-1224yd(E), 1-chloro-3,3,3-trifluoro-1-propyne, and HCFC-244bb.

The Examples 2, 4 and 6 are working fluids each obtained by extractive distillation refining using methanol of a crude composition obtained through (II) the hydrogen reduction of CFO-1214ya described above.

The trace components (X2) in the Examples 2, 4 and 6 each include HFC-254eb, HFO-1234ze(Z), fluorohydrocarbon represented by $C_4H_4F_4$, HCFC-244bb, HFC-245fa, CFO-1215xc, FC-227ca, HCFO-1224xe, HCFO-1224yd(E), and methanol.

Note that the working fluids of the Examples 1 to 6 were used as working fluids as they were without any other impurities being blended. In each of the Examples 7 to 16, the working fluid of the Example 1 or the Example 2 to which at least one kind of an acid content, a chlorine ion source, metal powder as an evaporation residue, air, and water was blended was used as the working fluid. The acid content contained in each of the working fluids was analyzed by an acid-base titration method, the chlorine ion therein was analyzed by a silver nitrate turbidimetry, and the evaporation residue (metal powder) therein was analyzed by a mass measuring method after a sample was evaporated. Further, the moisture content was measured by the Karl Fischer coulometric titration method, and the content of the air was measured by gas chromatography.

HF as the acid content and HCl as the chlorine ion source were weighed in a syringe so as to have the predetermined concentrations with respect to the mass of the working fluid and were added. The moisture was weighed in a syringe so as to have the predetermined concentration with respect to the mass of the working fluid and was added. The metal powder as the evaporation residue was weighed so as to have the predetermined concentration with respect to the mass of the working fluid and was added. Further, in a case where the air was blended, the air adjusted so as to have an 80% by volume nitrogen concentration and a 20% by volume oxygen concentration was sealingly filled so as to have the predetermined concentration with respect to the mass of the working fluid.

[Heat Stability Test]

Each of the working fluids in the Examples 1 to 16 and totally three sheets of SS400, Cu, and Al metal pieces, one sheet per each, whose side had a length of 20 mm×30 mm and whose thickness was 2 mm were put into a 200 mL stainless pressure-resistant vessel. Here, an amount of each of the working fluids blended is 50 g.

Next, the hermetic pressure-resistant vessel was kept in a thermostatic oven (Perfect Oven PHH-202 manufactured by ESPEC CORP.) at 175° C. for fourteen days, as the heat stability test. Regarding each of the working fluids after the test, an amount of the acid content was analyzed as follows.

(Measurement of Amount of Acid Content)

The pressure-resistant vessel after the above-described test was left standing still until its temperature became a room temperature. A set of four absorption bottles which were each filled with 100 ml pure water and were connected in series by pipes was prepared. The set of the connected absorption bottles each filled with the pure water was connected to the pressure-resistant vessel whose temperature had become the room temperature, a valve of the pressure-resistant vessel was gradually opened, a working fluid gas was introduced into the water of the absorption bottles, and the acid content contained in the working fluid gas was extracted.

The waters in the first and second absorption bottles after the extraction were mixed, and one drop of indicator (BTB: bromothymol blue) was added to the resultant water, and the water was titrated using 1/100N-NaOH alkali standard solution. At the same time, the waters in the third and fourth absorption bottles were mixed, and the resultant water was similarly titrated to be used as a measurement blank. From measurement values of these and a value of the measurement blank, the acid content contained in the working fluid after the test was found as an HCl concentration.

Criteria for the evaluation was as follows.

◯; The acid content is less than 2 ppm.

Δ; The acid content is 2 ppm or more and less than 10 ppm.

x; The acid content is 10 ppm or more.

The results are shown in Table 1. In Table 1, "<0.0001" indicates less than a detection limit (0.0001 mass %). In "Total of trace components (X)", a total amount (mass %) of the trace components (X) including a component with the detection limit is indicated by a numeral down to the second decimal place.

TABLE 1

| Example | HCFO-1224yd (Z) [mass %] | HCFO-1224yd (E) | HCFC-244bb | HCFO-1224xe | HFO-1234yf | 1-chloro-3,3,3-trifluoro-1-propyne | HFC-254eb | HFO-1234ze (Z) | $C_4H_4F_4$ | HFC-245fa | CFO-1215xc |
|---|---|---|---|---|---|---|---|---|---|---|---|
| | | Common to (X1) (X2) | | | | Trace component (X1) | Trace component (X2) | | | | |
| 1 | 99.4 | 0.36 | 0.085 | 0.001 | 0.07 | 0.001 | <0.0001 | <0.0001 | <0.0001 | <0.0001 | <0.0001 |
| 2 | 99.6 | 0.004 | 0.10 | 0.01 | <0.0001 | <0.0001 | 0.01 | 0.005 | 0.19 | 0.003 | 0.0004 |
| 3 | 98.8 | 0.79 | 0.15 | 0.003 | 0.13 | 0.002 | <0.0001 | <0.0001 | <0.0001 | <0.0001 | <0.0001 |
| 4 | 99.2 | 0.008 | 0.22 | 0.06 | <0.0001 | <0.0001 | 0.02 | 0.009 | 0.34 | 0.005 | 0.001 |
| 5 | 97.9 | 1.43 | 0.35 | 0.005 | 0.23 | 0.005 | <0.0001 | <0.0001 | <0.0001 | <0.0001 | <0.0001 |
| 6 | 98.2 | 0.009 | 0.21 | 0.06 | <0.0001 | <0.0001 | 0.02 | 0.011 | 0.32 | 0.005 | 0.001 |
| 7 | 98.0 | 0.35 | 0.084 | 0.001 | 0.07 | 0.001 | <0.0001 | <0.0001 | <0.0001 | <0.0001 | <0.0001 |
| 8 | 98.2 | 0.004 | 0.1 | 0.01 | <0.0001 | <0.0001 | 0.011 | 0.005 | 0.19 | 0.003 | 0.0003 |
| 9 | 99.4 | 0.36 | 0.085 | 0.001 | 0.07 | 0.001 | <0.0001 | <0.0001 | <0.0001 | <0.0001 | <0.0001 |
| 10 | 99.6 | 0.004 | 0.1 | 0.01 | <0.0001 | <0.0001 | 0.011 | 0.005 | 0.19 | 0.003 | 0.0003 |
| 11 | 99.4 | 0.36 | 0.085 | 0.001 | 0.07 | 0.001 | <0.0001 | <0.0001 | <0.0001 | <0.0001 | <0.0001 |
| 12 | 99.6 | 0.004 | 0.1 | 0.01 | <0.0001 | <0.0001 | 0.011 | 0.005 | 0.19 | 0.003 | 0.0003 |
| 13 | 99.4 | 0.36 | 0.085 | 0.001 | 0.07 | 0.001 | <0.0001 | <0.0001 | <0.0001 | <0.0001 | <0.0001 |
| 14 | 99.6 | 0.004 | 0.1 | 0.01 | <0.0001 | <0.0001 | 0.011 | 0.005 | 0.19 | 0.003 | 0.0003 |
| 15 | 99.4 | 0.36 | 0.085 | 0.001 | 0.07 | 0.001 | <0.0001 | <0.0001 | <0.0001 | <0.0001 | <0.0001 |
| 16 | 99.6 | 0.004 | 0.1 | 0.01 | <0.0001 | <0.0001 | 0.011 | 0.005 | 0.19 | 0.003 | 0.0003 |

| Example | FC-227ca | Methanol | Total of trace components (X) (mass %) | Acid content | Chlorine ion | Evaporation Residue | Air | Moisture | Heat stability evaluation |
|---|---|---|---|---|---|---|---|---|---|
| 1 | <0.0001 | <0.0001 | 0.52 | 0.5 | 0.2 | 10 | 1000 | 20 | ○ |
| 2 | 0.001 | 0.0001 | 0.32 | 0.5 | 0.2 | 10 | 1000 | 20 | ○ |
| 3 | <0.0001 | <0.0001 | 1.08 | 0.5 | 0.2 | 10 | 1000 | 20 | Δ |
| 4 | 0.002 | 0.0001 | 0.67 | 0.5 | 0.2 | 10 | 1000 | 20 | Δ |
| 5 | <0.0001 | <0.0001 | 2.02 | 0.5 | 0.2 | 10 | 1000 | 20 | x |
| 6 | 0.001 | 1.10 | 1.74 | 0.5 | 0.2 | 10 | 1000 | 20 | x |
| 7 | <0.0001 | <0.0001 | 0.51 | 0.5 | 0.2 | 10 | 15000 | 20 | Δ |
| 8 | 0.001 | 0.0001 | 0.32 | 0.5 | 0.2 | 10 | 15000 | 20 | Δ |
| 9 | <0.0001 | <0.0001 | 0.52 | 0.5 | 0.2 | 10 | 1000 | 100 | Δ |
| 10 | 0.001 | 0.0001 | 0.32 | 0.5 | 0.2 | 10 | 1000 | 100 | Δ |
| 11 | <0.0001 | <0.0001 | 0.52 | 1.0 | 0.5 | 10 | 1000 | 20 | Δ |
| 12 | 0.001 | 0.0001 | 0.32 | 1.0 | 0.5 | 10 | 1000 | 20 | Δ |
| 13 | <0.0001 | <0.0001 | 0.52 | 3.5 | 3.00 | 10 | 1000 | 20 | Δ |
| 14 | 0.001 | 0.0001 | 0.32 | 3.5 | 3.00 | 10 | 1000 | 20 | Δ |
| 15 | <0.0001 | <0.0001 | 0.52 | 0.5 | 0.2 | 100 | 1000 | 20 | Δ |
| 16 | 0.001 | 0.0001 | 0.32 | 0.5 | 0.2 | 100 | 1000 | 20 | Δ |

The working fluid for heat cycle of the present invention is applicable to freezing and cold-storage equipment (a built-in-type showcase, a separate-type showcase, a refrigerator for industrial use, a vending machine, an ice machine, and the like), an air-conditioning apparatus (a room air-conditioner, a store package air-conditioner, a building package air-conditioner, a facility package air-conditioner, a gas engine heat pump, a train air-conditioner, an automotive air-conditioner, and the like), a power generation system (waste heat recovery power generation and the like), and a heat transport apparatus (heat pipe and the like).

What is claimed is:

1. A working fluid for heat cycle, comprising: (Z)-1-chloro-2,3,3,3-tetrafluoropropene; and an impurity comprising 2-chloro-1,1,1,2-tetrafluoropropane in an amount of 0.01 to 0.1 mass %.

2. The working fluid for heat cycle according to claim 1, wherein a content ratio of the (Z)-1-chloro-2,3,3,3-tetrafluoropropene to the total amount of the working fluid for heat cycle is 20 mass % or more.

3. The working fluid for heat cycle according to claim 1, further comprising at least one selected from the group consisting of hydrofluorocarbon, hydrofluoroolefin, and hydrochlorofluoroolefin.

4. The working fluid for heat cycle according to claim 1, wherein the impurity further comprises an acid content, and a content ratio of the acid content to the total amount of the working fluid for heat cycle is less than 1 mass ppm.

5. The working fluid for heat cycle according to claim 1, wherein the impurity further comprises a chlorine ion, and a content ratio of the chlorine ion to the total amount of the working fluid for heat cycle is 3 mass ppm or less.

6. The working fluid for heat cycle according to claim 1, wherein the impurity further comprises an evaporation residue, and a content ratio of the evaporation residue to the total amount of the heat cycle is 15 mass ppm or less.

7. The working fluid for heat cycle according to claim 1, wherein the impurity further comprises moisture, and a content ratio of the moisture to the total amount of the working fluid for heat cycle is 20 mass ppm or less.

8. The working fluid for heat cycle according to claim 1, wherein the impurity further comprises air, and a content ratio of the air to the total amount of the working fluid for heat cycle is less than 15000 mass ppm.

9. The working fluid for heat cycle according to claim 1, wherein the total content ratio of the trace component to a total amount of the working fluid for heat cycle is 4 mass ppm to 1.5 mass %.

10. The working fluid for heat cycle according to claim 1, wherein the impurity further comprises 1-chloro-3,3,3-trifluoro-1-propyne in an amount of 0.0001 to 0.001 mass % relative to a total amount of the working fluid.

* * * * *